United States Patent [19]

Rega

[11] 4,285,747
[45] Aug. 25, 1981

[54] METHOD FOR MANUFACTURING A PRODUCT HAVING ELASTIC MEANS DISPOSED IN THE TRANSVERSE DIRECTION

[75] Inventor: John F. Rega, Milltown, N.J.

[73] Assignee: Johnson & Johnson Baby Products Company, New Brunswick, N.J.

[21] Appl. No.: 137,938

[22] Filed: Apr. 7, 1980

Related U.S. Application Data

[62] Division of Ser. No. 86,219, Oct. 18, 1979, Pat. No. 4,240,866.

[51] Int. Cl.³ .................. A61F 13/16; A32B 31/10; B32B 31/18
[52] U.S. Cl. .................. 156/164; 156/229; 156/265; 156/269; 156/297; 156/302; 156/494; 156/552
[58] Field of Search .................. 128/287, 290 R; 156/163, 164, 229, 264, 269, 297, 298, 302, 494, 552, 265

[56] References Cited

U.S. PATENT DOCUMENTS

| | | | |
|---|---|---|---|
| 3,560,292 | 2/1971 | Butter | 156/160 |
| 3,728,191 | 4/1973 | Wierzba et al. | 156/552 |
| 3,810,811 | 5/1974 | Bosse | 156/552 |
| 3,897,293 | 7/1975 | Babcock | 156/552 |
| 4,050,462 | 9/1977 | Woon et al. | 128/290 R |
| 4,074,716 | 2/1978 | Schaar | 128/287 |
| 4,081,301 | 3/1978 | Buell | 156/164 |
| 4,239,578 | 12/1980 | Gore | 156/164 |

Primary Examiner—Jerome W. Massie

[57] ABSTRACT

A method for adhering the end portions of an unstretched elastic member transverse of a web while the web is foreshortened in the transverse direction, returning the foreshortened web to its original dimension and adhering the stretched central portion of the elastic member to the web, and severing the web intermittently to produce individual products having transversely extending elastic means.

19 Claims, 8 Drawing Figures

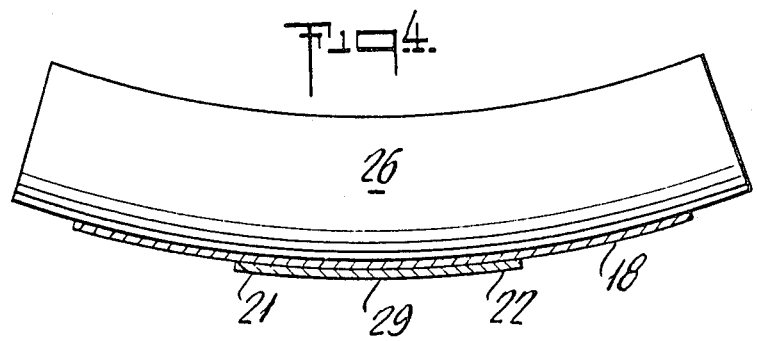
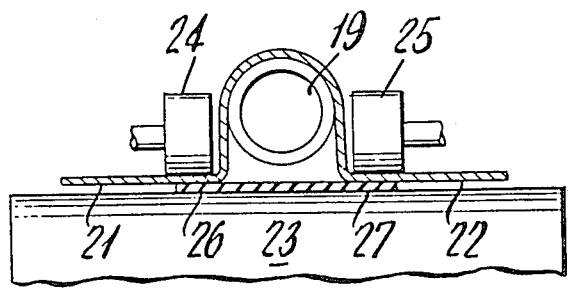
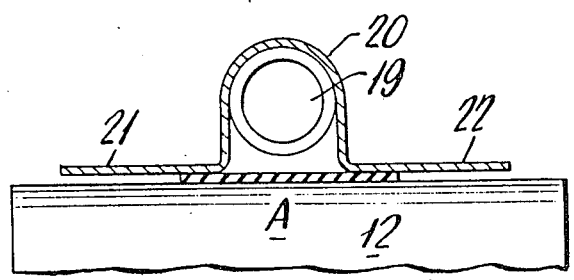
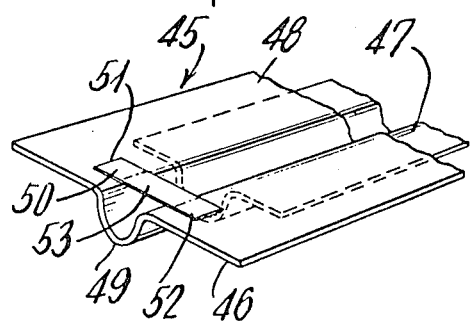
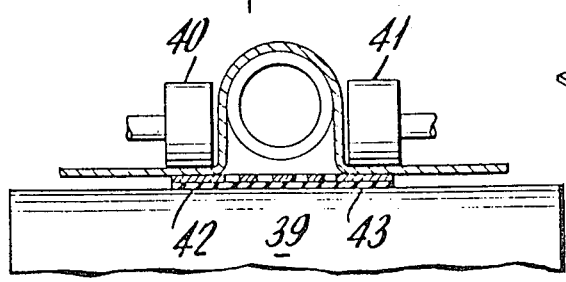
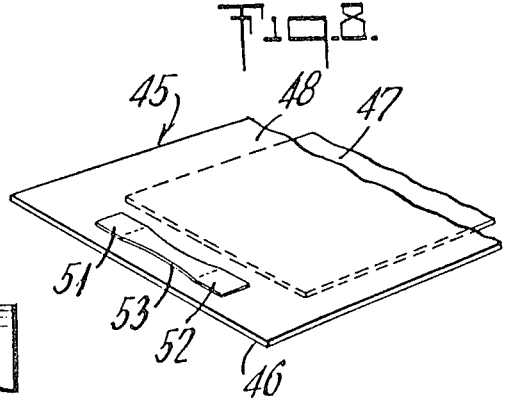

METHOD FOR MANUFACTURING A PRODUCT HAVING ELASTIC MEANS DISPOSED IN THE TRANSVERSE DIRECTION

This is a division of application Ser. No. 86,219, filed Oct. 18, 1979, now U.S. Pat. No. 4,240,866.

BACKGROUND OF THE INVENTION

The present invention relates to methods and apparatus for inserting an elastic member in the transverse direction of a product, and more specifically to methods and apparatus for placing elastic members in the waist-encircling portion of a disposable diaper.

Over the years, there have been a number of products which have an elastic member disposed in the transverse direction of the product, such as plastic pants, training pants, and the like. The elastic members may be sewn or adhered to the product in various manners as are well known in the art. Recently, there have come on the market a number of disposable diapers, which have elastic members inserted in the longitudinal direction of the product to make the leg-encircling portion of the diaper elastic. There are also a number of U.S. Patents which describe such products and methods for their manufacture such as U.S. Pat. Nos. 3,860,003; 4,050,462, and 4,081,301.

There are a number of U.S. Patents which describe elastic means disposed in the waist-encircling portion of a diaper or other techniques for providing stretch in the waist of the diaper or similar product; for example, see U.S. Pat. Nos. 3,920,018; 3,951,150; 3,990,450; 3,995,638; 4,036,233 and 4,041,949. To the best of my knowledge, none of the products having elastic waistband areas as described in these patents has enjoyed any commercial success. It is believed a primary reason for this lack of success is that no efficient, economical method has been discovered for inserting the elastic member in a suitable position in a diaper so as to render the waist-encircling portion of the diaper stretchable.

What I have discovered is a simple, economical, efficient, fast method for inserting elastic members transverse of a continuous web.

SUMMARY OF THE PRESENT INVENTION

What I have discovered is a method of applying an elastic member transverse of a continuously moving web to gather selected transverse portions of the web. In my method, the web is foreshortened in its transverse direction and while so foreshortened a preferably unstretched elastic member is adhered to the web to span the foreshortened area.

In a particular embodiment, the center of the web is disposed out of the plane of the side portions of the web and while so disposed, an elastic member is adhered to the side portions spanning the center portion. The foreshortened or the transversely reduced web is returned to its original transverse dimension and in so doing the unadhered center portion of the elastic member is stretched and may then be adhered to the straightened web. The web with elastic members thereon may then be severed as desired to produce one or more individual articles.

In a specific embodiment of the present invention, a continuous laminate of diaper stock which comprises an impervious film backing member, spaced apart absorbent pads disposed on said backing, and a continuous pervious facing member is produced. The facing and backing members are adhered to each other along their longitudinal side portions and are also adhered to each other in the transverse portion between adjacent absorbent pads. Such a laminated material is well known in the art and is usually cut or separated between adjacent absorbent pads and then folded in various manners to produce disposable diapers. In a specific method of the present invention, the laminate, prior to being cut into individual diaper portions, is passed over a bowing member or shoe which displaces the center portion of the laminate out of the plane of the continuously moving laminate while allowing the side portions to remain in that plane. In the preferred embodiment, the center portion is disposed in a direction away from the film backing side of the laminate and while so disposed, an elastic member is adhered to the film backing. Each end of the elastic member is adhered to a side portion of the film backing so that the center of the elastic member spans the center portion of the laminate which is disposed out of the plane of the web. The elastic member may have a pressure-sensitive adhesive applied to one surface and that surface is easily adhered to the side portions by the application of pressure. Once adhered, the laminate is passed over a bowed roll to straighten or pull the laminate in the transverse direction and return the laminate to its original transverse dimension. Such bowed rolls are well known in the art. While being pulled in the transverse direction, the center portion of the elastic member is stretched while the end portions remain unstretched but adhered to the film backing. Upon stretching to the full transverse direction of the continuous laminate, the center portion is pressed to the film backing and adhered thereto. Individual diaper blanks are then severed from the laminate.

The diaper blanks are folded and packaged as is well known in the art.

The invention will be more fully described in conjunction with the following drawings wherein:

FIG. 2 is a cross-sectional view taken along line 2—2 of FIG. 1;

FIG. 3 is a cross-sectional view taken along line 3—3 of FIG. 1;

FIG. 4 is a cross-sectional view taken along line 4—4 of FIG. 1;

FIG. 6 is a cross-sectional view taken along line 6—6 of FIG. 5;

FIG. 7 is a perspective view of one end of a diaper product which is foreshortened in the transverse direction and has an elastic member spanning the foreshortened portion; and FIG. 8 is a perspective view of the diaper of FIG. 7 which has been returned to its original transverse dimension.

DETAILED DESCRIPTION OF THE PREFERRED EMBODIMENTS OF THE PRESENT INVENTION

Figure 1:
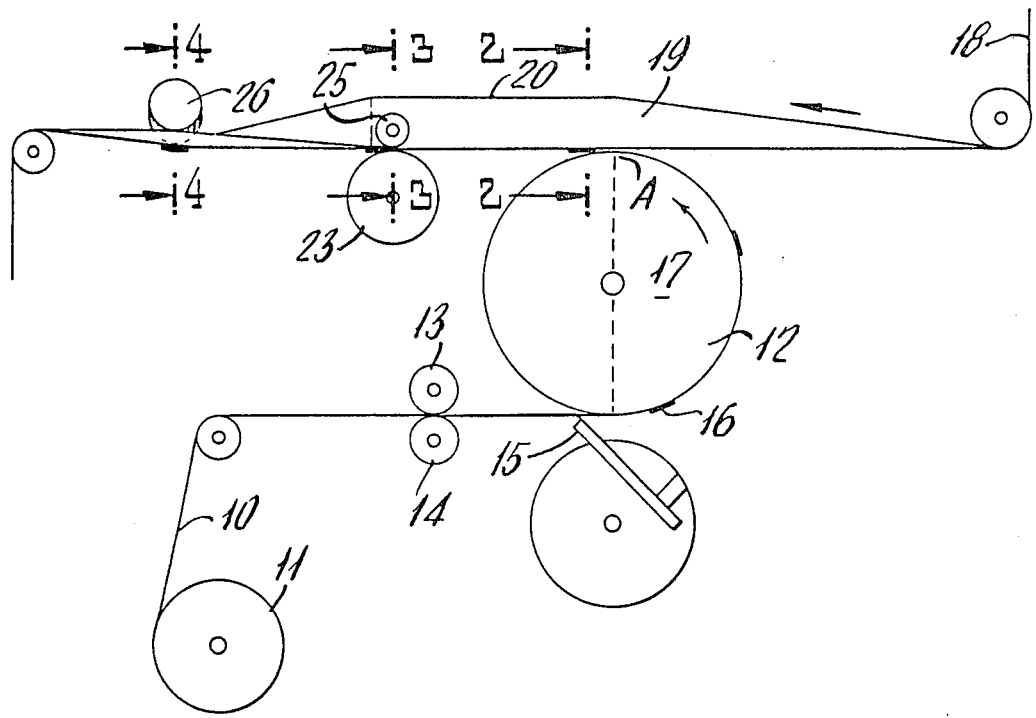
FIG. 1 is a schematic view in cross-section of one form of apparatus for carrying out the method of the present invention.

Referring to the drawings, FIG. 1 shows one form of apparatus for applying elastic members in accordance with the present invention. As shown in the drawing, elastic material 10 is supplied from a supply roll 11 and is fed to a rotating anvil-vacuum roll 12 by a pair of drive rolls 13 and 14. The movement of the elastic material is controlled by the drive rolls which advance the material a predetermined distance beyond the line where the cutter 15 meets the periphery of the anvil-vacuum roller. At this point, the cutter severs the appropriate length of the elastic material, and the elastic member 16 is held by the vacuum portion 17 of the anvil-vacuum roll and accelerated to the peripheral surface speed of that roll. The elastic member is carried by the vacuum portion to the application position A. In this embodiment, the elastic member has a pressure-sensitive adhesive mass on the surface disposed away from the anvil-vacuum roll for adhering the member to an appropriate web material. Diaper stock or other appropriate web or sheet material 18 is fed tangentially past the anvil-vacuum roll at a spot substantially adjacent the area where the vacuum is removed. The diaper stock is conveyed over a suitable chute 19 which causes the central portion 20 of the diaper stock to be displaced out of the plane of the diaper stock. This chute causes the longitudinal side portions 21 and 22 of the diaper stock to be urged towards each other. This is more clearly shown in FIG. 2 which is a cross-section of the chute 19 with the diaper stock 18 disposed about the chute in an appropriate configuration. At the application point A, the vacuum is removed from the elastic member and the pressure-sensitive adhesive attaches the elastic member to the diaper stock spanning the portion of the diaper stock disposed out of the original plane of the stock and around the chute. The diaper stock and elastic member are moved along to a pressure applying position. As is more clearly shown in FIG. 3, the diaper stock 18, in its position about the chute 19, passes over a back-up roller 23. The longitudinal side portions 21 and 22 of the stock are urged or pressed against the back-up roller by the pressing rollers 24 and 25. This pressure securely adheres each end 26 and 27 of the elastic member 16 in an unstretched state to the diaper stock. The diaper stock is continued to be conveyed and moved off the chute 19 and then over a bowed roll 26. The bowed roll expands or stretches the diaper stock back to its original flat position; in fact, to a concave position as shown in FIG. 4, and in so doing, stretches the elastic member in the center portion 29. This action also urges the elastic member against the diaper stock and adheres the center portion in a stretched condition to the diaper stock. The diaper stock or web may then be further processed as is well known in the art by separating intermittent lengths and folding and packing them as in the standard manufacture of diapers.

Figure 5:
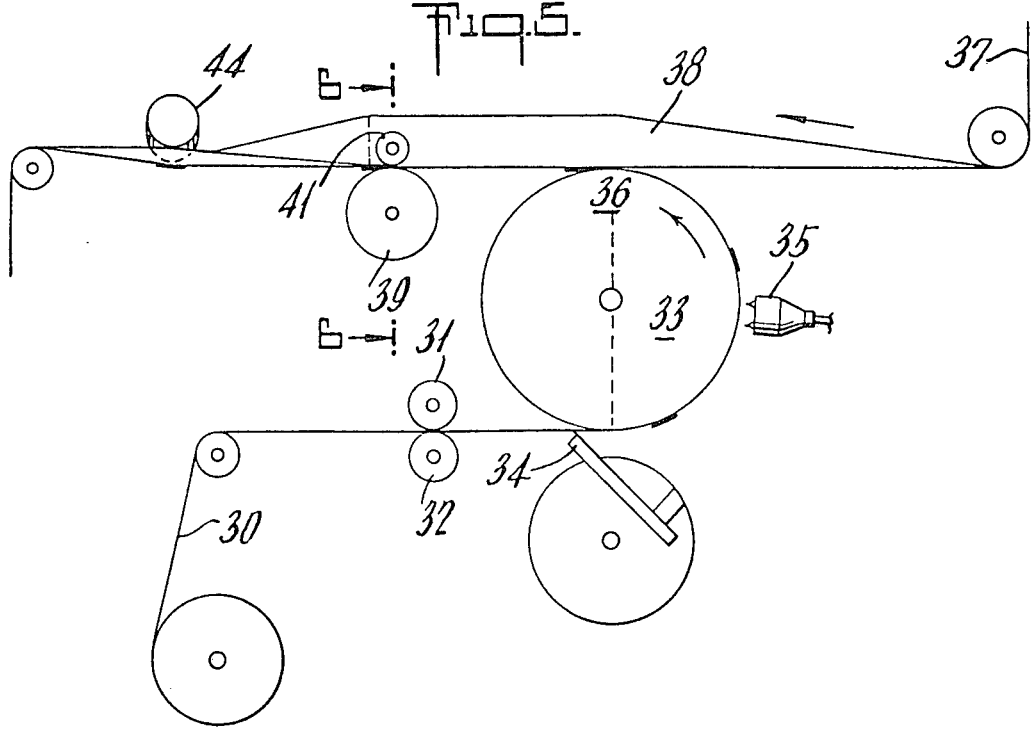
FIG. 5 is a schematic view of another apparatus for carrying out the method of the present invention.

In FIG. 5, there is shown a modified form of apparatus for applying elastic members in accordance with the present invention. In this embodiment, the elastic member 30 in the form of a rubber material is intermittently fed through a pair of drive rollers 31 and 32 to the surface of an anvil-vacuum roll 33. A knife cutter roll 34 cuts an appropriate length of the elastic member which is then carried on the surface of the roll 33 by vacuum appropriate applied. Suitable hot melt or other adhesive is applied to the outer surface of the cut elastic member by nozzle 35 and the cut elastic member with the adhesive thereon is carried to the application zone 36. As described, in conjunction with FIGS. 2-4, the diaper stock 37 is conveyed in a path adjacent the surface of the anvil-vacuum roll and substantially at the point where the vacuum is removed from holding the elastic member. The diaper stock is conveyed over the chute 38 to dispose a center portion of the diaper stock out of the plane of the diaper while urging the longitudinal side margins of the diaper towards each other in the plane of the stock. The elastic member is urged against the diaper stock and the elastic member at its ends adhered to the diaper stock. As is more clearly seen in FIG. 6, the diaper stock with the elastic ribbon adhered thereto is passed between the back-up roll 39 and two pressure-applying rolls 40 and 41, one on each side of the chute, which press the ends 42 and 43 of the elastic member to the diaper stock and secures them thereto. The diaper stock is removed and conveyed away from the chute over a bowed roller 44 and the diaper stock stretched to a flattened, concave configuration which stretches the unadhered center portion of the elastic member and adheres the center portion to the diaper stock. The diaper stock may then be processed, that is, folded, cut, and packaged as individual diapers as is well known in the art.

FIG. 7 shows one specific diaper construction. Broadly, the diaper 45 comprises a water pervious facing sheet 46, suitable absorbent pad 47 of wood pulp or layers of tissue, and an impervious backing sheet 48, usually a polyolefin film. In this embodiment, the facing and backing sheet are co-extensive and the absorbent panel is smaller and fits within the perimeter of the facing and backing sheets. The central portion 49 of the diaper is disposed out of the plane of the diaper and that disposed portion has an elastic member 50 spanning the disposed portion. The elastic member in this embodiment is positioned against the impervious backing sheet or film. The elastic member is adhered to the backing sheet at the ends 51 and 52 of the elastic member with the center of the elastic member 53 unadhered at this time. As is shown in FIG. 8, upon returning the diaper to a uniform flat plane, the elastic member between its adhered ends is stretched and urged against the impervious backing member in the stretched portion to form a waist-encircling portion of a diaper that has stretchability or elasticity.

The elastic member may be made from rubber, either natural or synthetic, or other well known elastic, thermoplastic film materials. Elastic members may be adhered to the diaper either by pressure sensitive adhesive, standard adhesive latices, hot adhesives, and the like. The size of the elastic member, that is, the width and length, will depend on how much elasticity is desired in the transverse portion of the product and, of course, the size of the diaper product itself.

From the foregoing discussion, it will be appreciated that the present invention provides a new improvement, particularly adaptable for disposable diapers, to provide elastic waistband portions utilizing a simple and economical method and apparatus so that the fabrication and production of the diaper itself is more economical and produces a suitably functional diaper. Accordingly, others skilled in the art may make modifications to the disclosed embodiment without departing from the spirit and scope of the present invention as pointed out in the appended claims.

It is claimed:

1. The method of applying an elastic member transverse of a continuously moving web to render selected transverse portions of the web stretchable comprising, positioning the web in a plane, disposing the central longitudinal portion of said web out of said plane while the longitudinal side portions of the web remain in said plane; adhering an elastic member to said side portions, said elastic member spanning said central longitudinal portion of the web, causing said central longitudinal portion of the web to be returned substantially to its original plane, thereby causing said elastic member spanning said central longitudinal portion to be stretched in a direction transverse of said moving web and adhering said stretched elastic portion to said central longitudinal portion of said web.

2. A method of applying an elastic member transverse of a continuously moving web to render selected transverse portions of said web stretchable comprising; (a) reducing the transverse dimension of said web by forming a longitudinally extending pleat in the central portion of said web, (b) adhering opposite ends of an elastic member in an unstretched state to longitudinal side portions of said web with the center of said elastic member spanning the longitudinally extending pleat; (c) diverging said side portions of the web to remove the pleat and stretch the center of said elastic member, and (d) adhering said stretched center portion of said elastic member to the central portion of said web.

3. A method of intermittently applying individual, discrete elastic members transverse of a continuously moving web to render spaced apart portions of the web stretchable in the transverse direction comprising: positioning the web in a plane, displacing the central longitudinal portion of said web out of said plane while the longitudinal side portions of the web remain in said plane; continuously feeding spaced apart, individual, discrete, elastic members adjacent the web with the ends of each elastic member being disposed adjacent opposite longitudinal side portions of the web and the center of the member spanning the central longitudinal portion of the web, adhering the unstretched end portions of the elastic member to the respective longitudinal side portions of the web, diverging the longitudinal side portions with respect to each other to return the web at least to its original plane to stretch the center portion of the elastic member and adhering said stretched portion to the web.

4. The method of claim 3 wherein the central longitudinal portion of the web is displaced out of the plane; in a substantially uniform semi-circular shape.

5. The method according to claim 3 wherein adhesive is applied to the elastic members before they are fed adjacent the web and the adhesive is used to secure the elastic member to the web.

6. The method according to claim 3 wherein the elastic members carry a pressure sensitive adhesive on one surface and that surface is disposed adjacent the web and adhered thereto.

7. The method according to claim 3 wherein the web is returned to a plane beyond its original plane so that it is curved in a direction opposite to the direction the center longitudinal portion was originally displaced to cause the stretched center portion of the elastic member to be urged against the central portion of the web.

8. The method according to claim 7 wherein the elastic members carry a pressure-sensitive adhesive on one surface and that surface is disposed adjacent the web and adhered thereto.

9. The method of manufacturing disposable diapers having stretchable waistband portions comprising: moving diaper stock comprising continuous and coextensive pervious and impervious web surfaces having spaced apart absorbent pads disposed therebetween, said webs being secured together along their longitudinal side margins and in spaces between said absorbent pads, in a plane; displacing the central longitudinal portion of the stock out of said plane while maintaining the longitudinal side portions of the stock in said plane; continuously feeding spaced apart, individual, discrete, unstretched elastic members adjacent the surface of the stock in alternate spaces between absorbent pads with the ends of each elastic member being disposed adjacent opposite longitudinal side margins of the stock and the center of said elastic member spanning the central longitudinal portion of the stock; adhering the unstretched end portion of said elastic member to the surface of the respective side portions of the stock; diverging the longitudinal side portions with respect to each other to return the stock to at least its original plane to stretch the center portion of the elastic member and adhere it to the surface of the stock; and transversely severing the diaper stock in the spaces between absorbent pads to produce individual disposable diapers.

10. The method according to claim 9 wherein the central longitudinal portion is displaced out of the plane in a substantially uniform semi-circular shape.

11. The method according to claim 9 wherein the unstretched elastic members are fed adjacent the surface of the stock to every space between absorbent pads.

12. The method according to claim 9 wherein adhesive is applied to the elastic members before they are fed adjacent the surface of the stock and the adhesive is used to secure the elastic member to the surface.

13. The method according to claim 9 wherein the elastic members carry a pressure-sensitive adhesive on one surface and that surface is disposed adjacent the surface of the stock and adhered thereto.

14. The method according to claim 9 wherein the stock is returned to a plane beyond its original plane so that it is curved in a direction opposite to the direction the center longitudinal portion was originally displaced to cause the stretched center portion of the elastic member to be urged against the central portion of the surface of the stock.

15. The method according to claim 14 wherein the elastic members carry a pressure-sensitive adhesive on one surface and that surface is disposed adjacent the surface of the stock and adhered thereto.

16. The method according to claim 9 wherein the surface of the stock to which the elastic members are adhered is the impervious web surface.

17. The method according to claim 16 wherein the elastic members carry a pressure-sensitive adhesive on one surface and that surface is disposed adjacent the surface of the stock and adhered thereto.

18. The method according to claim 16 wherein the stock is returned to a plane beyond its original plane so that it is curved in a direction opposite to the direction the center longitudinal portion was originally displaced to cause the stretched center portion of the elastic member to be urged against the central portion of the surface of the stock.

19. The method according to claim 18 wherein the elastic members carry a pressure-sensitive adhesive on one surface and that surface is disposed adjacent the surface of the stock and adhered thereto.

* * * * *